United States Patent [19]

Nunan

[11] 4,112,306
[45] Sep. 5, 1978

[54] NEUTRON IRRADIATION THERAPY MACHINE

[75] Inventor: Craig S. Nunan, Los Altos Hills, Calif.

[73] Assignee: Varian Associates, Inc., Palo Alto, Calif.

[21] Appl. No.: 748,020

[22] Filed: Dec. 6, 1976

[51] Int. Cl.² .................................................. G21G 4/02
[52] U.S. Cl. ..................................... 250/499; 328/234
[58] Field of Search ......................... 250/499; 328/234

[56] References Cited

U.S. PATENT DOCUMENTS

| 3,015,030 | 12/1961 | Jones | 250/269 |
|---|---|---|---|
| 3,175,131 | 3/1965 | Burleigh et al. | 328/234 |
| 3,868,522 | 2/1975 | Bigham et al. | 328/234 |
| 3,925,676 | 12/1975 | Bigham et al. | 250/499 |

*Primary Examiner*—Harold A. Dixon
*Attorney, Agent, or Firm*—Stanley Z. Cole; Leon F. Herbert; Edward H. Berkowitz

[57] ABSTRACT

In a neutron irradiation therapy machine for treating patients with a beam of high energy neutrons, a gantry is provided which supports a non-superconducting cyclotron proton accelerator and target for generating a neutron beam and which permits rotation of the accelerator and neutron beam around an axis of revolution coaxial with a patient treatment zone. A counter-weight is carried from the gantry in a diametrically opposed relation to the cyclotron and behind the support bearing for counter-weighting the cyclotron and its associated equipment rotationally and longitudinally. The cyclotron includes an enclosing magnetic return yoke having a re-entrant portion in axial alignment with the magnetic poles of the cyclotron for reducing the weight of the yoke. The enclosing magnetic return yoke, and any additional surrounding material such as boron loaded polyethylene and lead, provide radiation shielding to protect the patient. An alternative patient table is coaxially mounted of the gantry and supported from a rotor portion thereof via a bearing assembly so that the rotor rotates around the stationary patient table. A neutron beam stopper is carried from the rotator of the gantry in axial alignment with the neutron beam and diametrically opposed to the cyclotron for absorbing neutrons passing through the patient treatment zone. Evacuable radio frequency transmission lines are provided for feeding RF power to the cyclotron and which pass through the yoke and are connected in gas communication with a vacuum pump for evacuating the cyclotron via the intermediary of the RF transmission lines. The cyclotron accelerates a beam of charge particles, such as protons, to relatively high energy, as of 30 MeV, to bombard a target formed of first and second materials. The first target material has a relatively high yield for high energy neutrons at proton energies in excess of 15 MeV, whereas a second portion of the target has a low yield for neutrons at proton energies less than 15 MeV, for stopping the protons. Tungsten shielding elements are disposed surrounding the neutron producing target and other regions for attenuation of neutrons falling outside of the desired neutron beam lobe. An adjustable and rotatable neutron beam collimator is arranged for varying the orientation and cross sectional dimensions of the neutron beam as applied to the patient treatment zone.

26 Claims, 10 Drawing Figures

NEUTRON IRRADIATION THERAPY MACHINE

BACKGROUND OF THE INVENTION

The present invention relates in general to neutron irradiation therapy machines and more particularly to such machines employing a cyclotron for accelerating charged particles to a high energy for bombardment of a neutron generating target which is characterized by having a high yield of high energy neutrons and wherein the cyclotron is supported from a structure for rotation about a patient treatment zone.

DESCRIPTION OF THE PRIOR ART

Heretofore, neutron irradiation therapy machines have been proposed wherein a superconducting cyclotron deuteron accelerator has been carried from a gantry for revolution about the patient treatment zone for treatment of the patient with a neutron generated beam through a multiplicity of treatment ports. Such a neutron therapy machine is disclosed in U.S. Pat. No. 3,925,676 issued Dec. 9, 1975.

In this prior art machine, the magnetic field for the cyclotron was generated by means of a superconducting electromagnet thereby reducing the weight of the cyclotron magnet so that it could be supported from a gantry for rotation about a patient treatment zone. The problem with using a superconducting magnet is that it requires a source of liquid helium for cooling the superconducting coils to a superconducting temperature. The requirement to maintain a large piece of equipment at liquid helium temperature for long periods of time in a hospital environment has disadvantages which it is desired to avoid.

However, when a shift is made from a superconducting magnet to a conventional electromagnet, the weight of the magnet increases by approximately an order of magnitude, i.e., from approximately 4 tons to 24 tons, thereby substantially complicating the design of the necessary gantry and other components.

Also, in this prior art neutron irradiation therapy machine, means were not provided for stopping the neutron beam after passage through the patient treatment zone, thereby causing severe shieldinbg problems for the patient treatment room. In addition, separate vacuum pump-out tubes passed through the closed yoke of the cyclotron magnet, thereby permitting leakage of radiation through such pump-out tubes. Another problem with the prior art target is that with a proton beam it would produce a large yield of neutrons having relatively low energies and it is desirable to reduce the number of such neutrons generated or produced and which can produce a relatively high radiation dose in the skin and shallow tissue of the patient. In addition, the prior art neutron therapy machines utilized a fixed aperture in the yoke of the magnet for collimating the neutron beam. This is one method of collimating the beam but it is desirable to provide a collimator of a type which will permit stepless adjustment of the cross sectional dimensions and orientation of the neutron beam in the treatment region.

SUMMARY OF THE PRESENT INVENTION

The present invention employs a proton cyclotron, efficiently designed to minimize total weight while producing a neutron flux of relatively high mean energy. For example, a 25 MeV deuteron superconducting cyclotron of the prior art weighs 4.5 tons and would weigh about 100 tons for the same deuteron energy if the magnet were water cooled. The present invention employing 30 MeV protons instead of 25 MeV deuterons, is capable of achieving a higher mean energy neutron beam while limiting the water cooled cyclotron weight to about 24 tons, which is still light enough to permit gantry mounting.

The principal object of the present invention is the provision of an improved neutron irradiation therapy machine.

In one feature of the present invention, the weight of the cyclotron magnetic yoke is reduced by providing re-entrant yoke portions adjacent the respective pole portions of the magnet, thereby reducing the weight of the magnetic yoke.

In another feature of the present invention, the neutron irradiation therapy machine includes a cyclotron accelerator carried from a gantry for rotation about a patient treatment zone, such gantry including a counterweight diametrically and longitudinally supported from the gantry for counter-weighting the weight of the cyclotron.

In another feature of the present invention, a patient table, for supporting the patient in the patient treatment zone, is carried from the rotor portion of the gantry by means of a bearing assembly, thereby permitting the patient treatment table to remain stationary while the rotor of the gantry rotates about the patient table.

In another feature of the present invention, a neutron beam stopper is carried from the gantry in diametrically opposed relation to the cyclotron and in alignment with the neutron beam for absorbing the neutron beam after passage through the patient treatment zone, thereby reducing the required shielding for the patient treatment room.

In another feature of the present invention, the vacuum envelope of the cyclotron is pumped by a vacuum pump to a subatmospheric pressure via the intermediary of a radio frequency transmission line passing through the envelope, whereby the number of ports through the magnetic yoke of the cyclotron is reduced thereby reducing spurious radiation.

In another feature of the present invention, the target which is subject to bombardment with high energy charged particles to produce the neutron beam is formed of first and second materials, the first material providing a relatively high yield of high energy neutrons upon bombardment with high energy protons and the second portion of the target providing a relatively low neutron yield upon bombardment with protons of an energy below 15 MeV, whereby low energy protons are absorbed without generation of low energy neutrons for reducing the low energy neutron spectral constituent of the resultant neutron beam.

In another feature of the present invention, the neutron generating target is surrounded by a neutron shield having a charged particle beam entrance passageway and a neutron beam exit passageway therein, whereby spurious radiation from the target is shielded.

In another feature of the present invention, a neutron beam collimator is disposed in alignment with the lobe of neutron flux emanating from the target, such collimator being adjustable for varying the cross sectional area and/or orientation of the neutron beam as applied to the patient treatment zone.

Other features and advantages of the present invention will become apparent upon a perusal of the follow-

DESCRIPTION OF THE PREFERRED EMBODIMENTS

Figure 1:
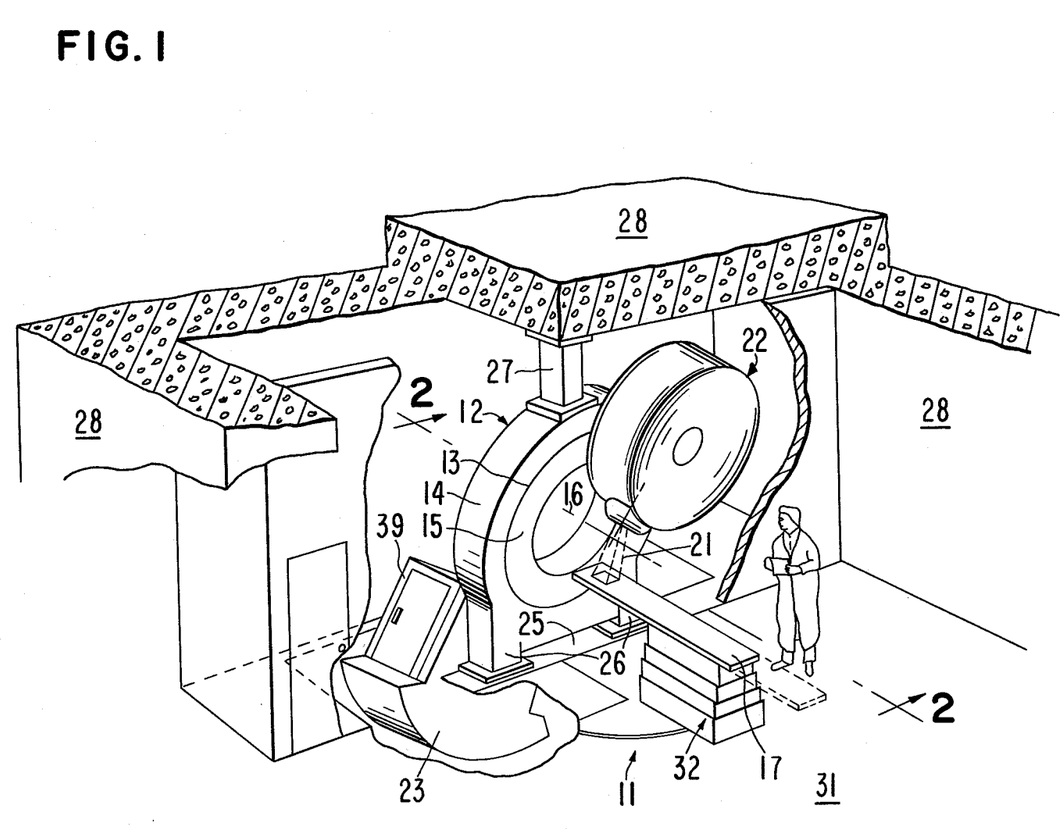
FIG. 1 is a perspective view, partially cut away, of a patient treatment room including a neutron irradiation therapy machine incorporating features of the present invention.
Figure 2:
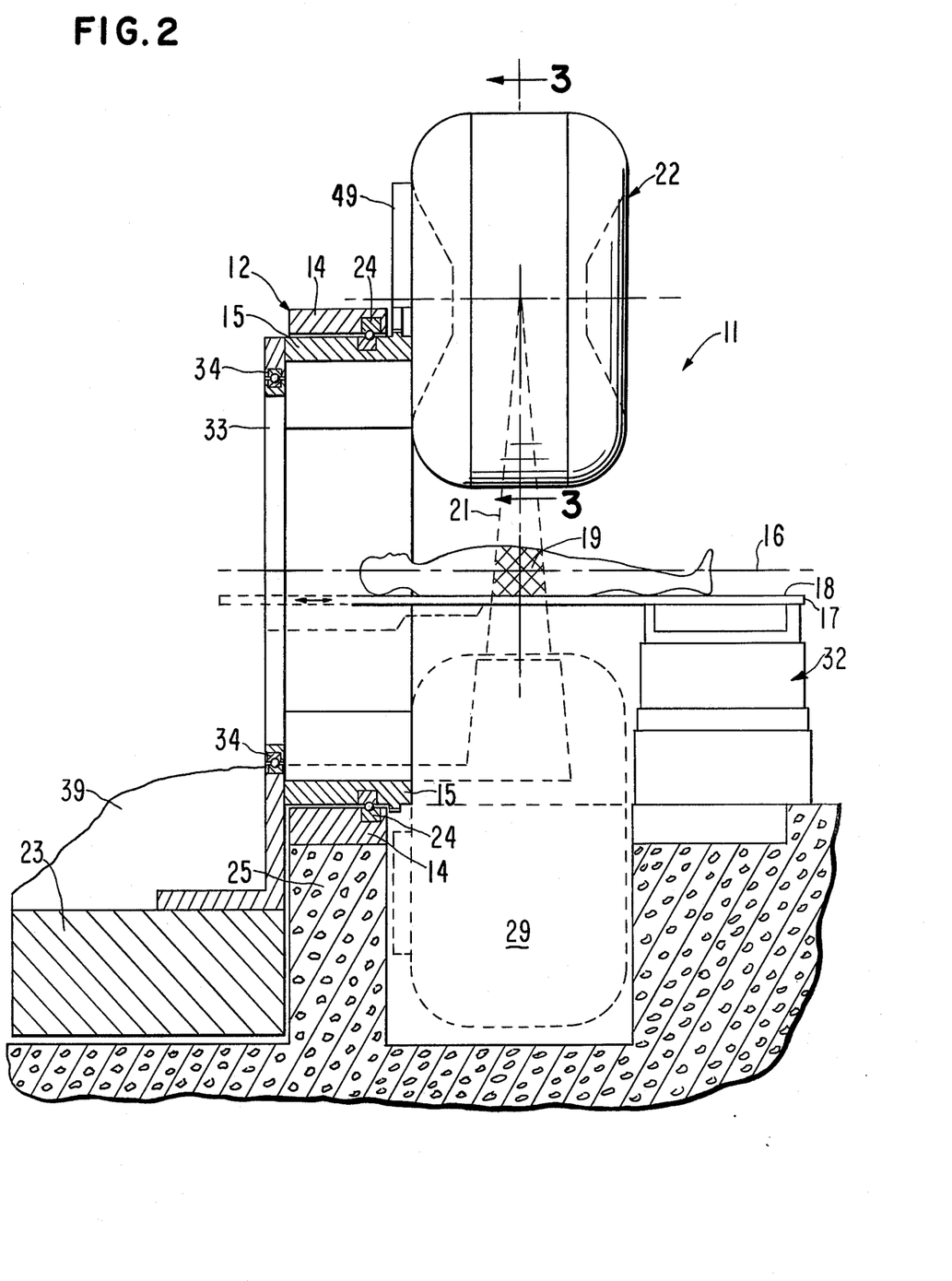
FIG. 2 is a side elevational view of the neutron irradiation therapy machine of the structure of FIG. 1 taken along line 2—2 in the direction of the arrows.

Referring now to FIGS. 1 and 2 there is shown the neutron irradiation therapy machine 11 incorporating features of the present invention. The machine 11 includes a gantry 12 including a main cylindrical bearing 13 having a stationary annular outer race or stator 14 and an inner rotatable race or rotor 15 for rotation about an axis of rotation 16 positioned just above a patient support table 17. The table 17 has a support plane 18 axially parallel to the axis of rotation 16 and is disposed a few inches below the axis of rotation 16 so that a patient treatment zone 19 is defined in the body of the patient in the region intersected by the axis of rotation 16 and a beam of high energy neutrons 21 emanating from a target within a cyclotron 22 carried from the rotor 15 of the gantry 12.

In a typical example, the cyclotron 22 has a weight of approximately 24 tons and a counter-weight 23 is coupled to the rotor 15 in diametrically opposed relation to the cyclotron 22 for counter balancing or counter-weighting the weight of the cyclotron 22. The cyclotron is carried from a first face of the rotor 15, whereas the counter-weight 23 is carried from the opposite face of the rotor 15 so as to place the center of gravity inside of the axial extent of the rotor 15. A bearing assembly 24 is placed on the transverse plane containing the center of gravity as shown in FIG. 2.

The stator 14 is fixedly secured to a base support 25 via a pair of pedestals 26, whereas the upper end of the stator 14 is fixedly secured to a ceiling or upper support via an upper support member 27. The gantry 12 and cyclotron 22 are contained within a shielded room having walls 28 made of concrete for absorbing and shielding other areas from the spurious radiation given off by the neutron therapy machine 11. The floor is recessed at 29 in the plane of rotation of the cyclotron 22 to permit clearance for the cyclotron 22 for rotation below the patient.

In one embodiment, the patient support table 17 is supported from the floor 31 via a table support structure 32, whereas in an alternative embodiment the patient support table 17 is supported from the rotor 15 via the intermediary of an annular or disc-shaped support member 33 disposed within the rotor 15 and supported therefrom via bearing assemblies 34, such that the rotor 15 is free to rotate about the stationary table support wall or member 33. This alternative support for the patient table 17 has the advantage that the table 17 can be precisely aligned with the accelerator 22 at the factory without having to align the table 17 and the table support 32 in the hospital where the treatment machine is installed. In addition, the alternative support leaves the treatment room floor area clear for personnel to set up the patient and it eliminates interference with the floor pit 29.

Figures 3, 4:
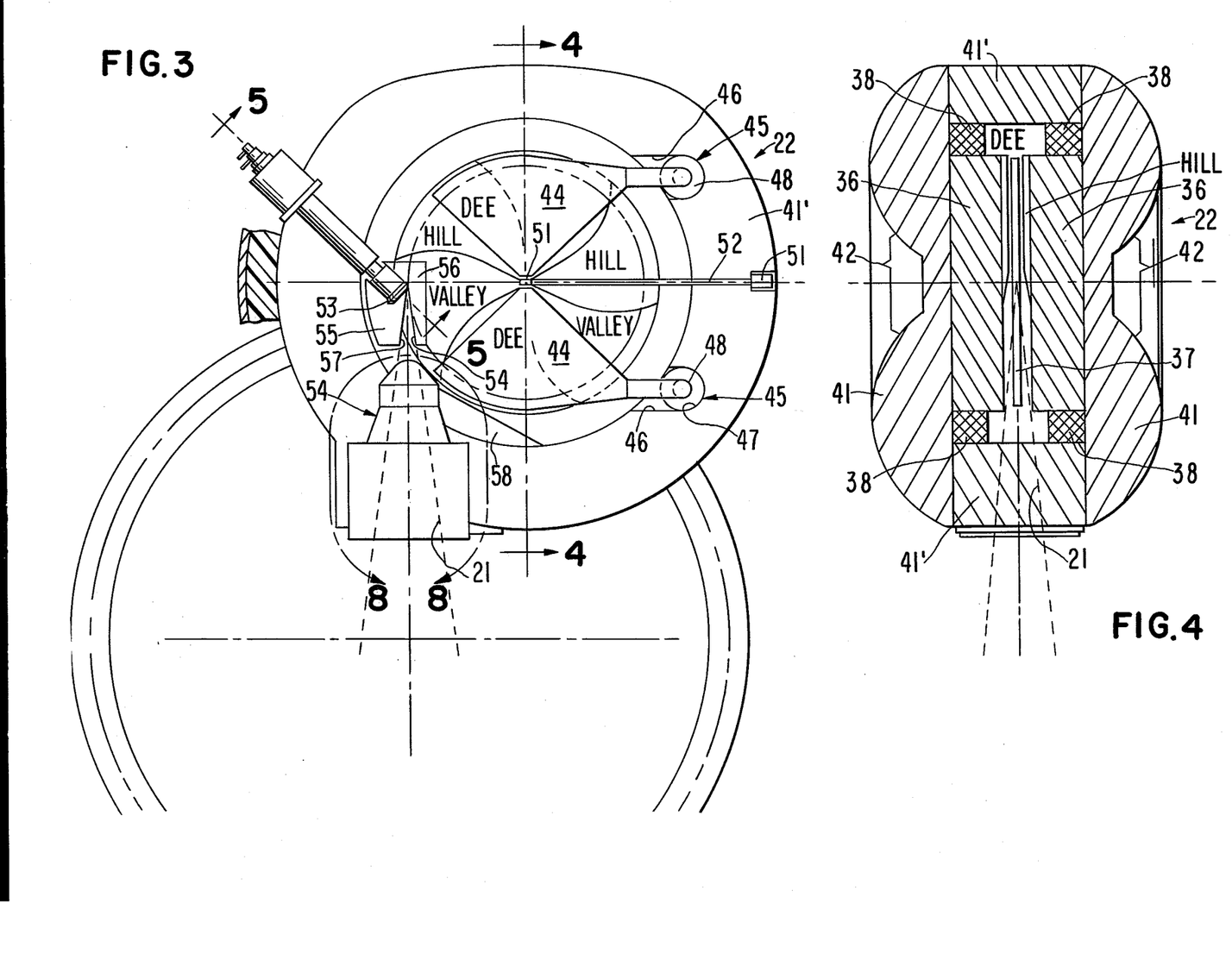
FIG. 3 is a cross sectional view of the structure of FIG. 2 taken along line 3—3 in the direction of the arrows.
FIG. 4 is a sectional view of the structure of FIG. 3 taken along line 4—4 in the direction of the arrows.

Referring now to FIGS. 3 and 4, the cyclotron 22 is described in greater detail. The cyclotron 22 includes a pair of cylindrical magnetic pole piece portions 36, as of soft iron, axially spaced apart to define a magnetic gap 37 in which charged particles, preferably protons, are accelerated in a spiral path to a high energy as of 30 MeV. The pole pieces 36 are energized to opposite polarities via a pair of ribbon coils 38 wound around the respective pole portions 36 and energized with electrical current from a suitable current supply carried within an equipment housing 39 affixed to the counter-weight 23 or as an alternative, carried within a cylindrical space within the rotor 15 of the gantry 12.

A generally toroidal shaped magnetic yoke 41, as of soft iron, encloses the pole pieces 36 and provides a low reluctance return flux path for the magnetic flux lines returning externally of the gap 37 around the coils 38. The end portions of the magnetic yoke 41 are provided with decreased thickness in a re-entrant section 42 in axial alignment with each of the poles 36 so as to reduce the weight of the yoke structure 41.

The cyclotron 22 is of conventional design including a pair of sector-shaped RF electrodes 44 positioned in the midplane of the gap 37 in opposed relation and supplied with RF power via a pair of RF coaxial transmission lines 45 passing axially through a generally cylindrical portion 41' of the magnetic yoke 41. The axially directed RF transmission lines 45 include a short 90° bend section 46 disposed generally in the midplane of the yoke for connecting the RF coaxial lines 45 to the respective electrodes 44. The RF transmission lines 45 include a hollow tubular outer conductor 47 and an inner conductor 48 and serve a second function of providing an exhaust tubulation interconnecting a high vacuum pump (not shown) such as a titanium ball sublimation pump carried within the cylindrical equipment compartment of the rotor 15 of the gantry 12 and an evacuable chamber defined within the interior of the magnetic yoke 41. Suitable RF transmission lines interconnect a source of RF power (not shown) similarly carried within the equipment compartment of the rotor 15. The vacuum pump and RF power source are connected to the RF transmission line 45 via the intermediary of an RF and vacuum manifold 49 (see FIG. 2) affixed to the cyclotron yoke 41.

Figure 7:
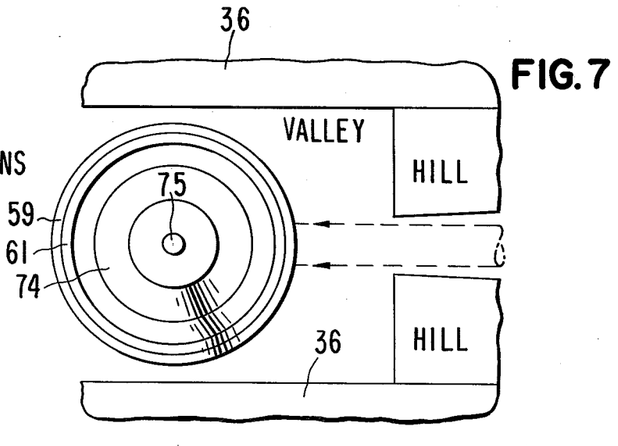
FIG. 7 is an end view of the structure of FIG. 6 taken along line 7—7 in the direction of the arrows.

An ion source 51 is supported through a radially directed bore 52 in the yoke 41 and emits suitable charged particles, such as protons into the central region of the electrodes 44. The charged particles are accelerated by the RF electric fields and guided and focused by the magnetic field produced between the magnetic poles 36. The cyclotron magnetic pole structure 36 is of conventional design wherein the poles 36 of the magnet structure are formed into hills and valleys, the hills and valleys having sector shapes, as illustrated in FIGS. 3, 4 and 7, in order to provide net focusing of the particle orbits while maintaining phase synchronism with the RF field as the particles gain in relativistic mass during acceleration.

The ions are accelerated in a spiral path to a relatively high energy, as of 30 MeV, near the periphery of the magnetic gap 37 and are directed into a target 53 for generating the beam 21 of high energy neutrons which thence pass through a variable collimator 54 to the patient treatment zone 19.

The neutrons are generated in a generally forward lobe, with about 5% intensity at 180° and about 10% intensity at 90° relative to 100% intensity at 0° on treatment beam axis. The neutron flux generated in the portions of the lobe outside the treatment beam cone is shielded by a primary collimator 55, a second shield 58, the poles and yoke of the magnet and any additional boron loaded polyethylene and lead surrounding the magnet yoke.

A primary neutron beam shield or collimator 55 is disposed surrounding the target 53 and comprises a block of neutron absorbing material, as of tungsten, having a radially directed arcuate slot 56 therein coplanar with the plane of acceleration of the particles which are to bombard the target 53. The slot 56 has a tangential back wall portion 57 to collimate and define one side edge of the neutron beam 21. The purpose of the primary beam collimator or shield 55 is to inhibit undesired spurious neutron radiation to confine the neutron irradiation as much as possible to the intended neutron beam path 21. A second tungsten shield 58 is disposed at the periphery of the inside cylindrical wall of the iron yoke 41' in a position coplanar with the magnetic gap 37 and coplanar with the plane of acceleration of the charged particles so as to provide neutron shielding in the forwardly direction from the target 53. The generally cylindrical portion 41' of the magnetic yoke has a thinner radial wall thickness on the side opposite to the collimator 54 so that the weight of the yoke is reduced on the side thereof where the thickness of the yoke need not be employed for so much radiation shielding.

Figure 5:
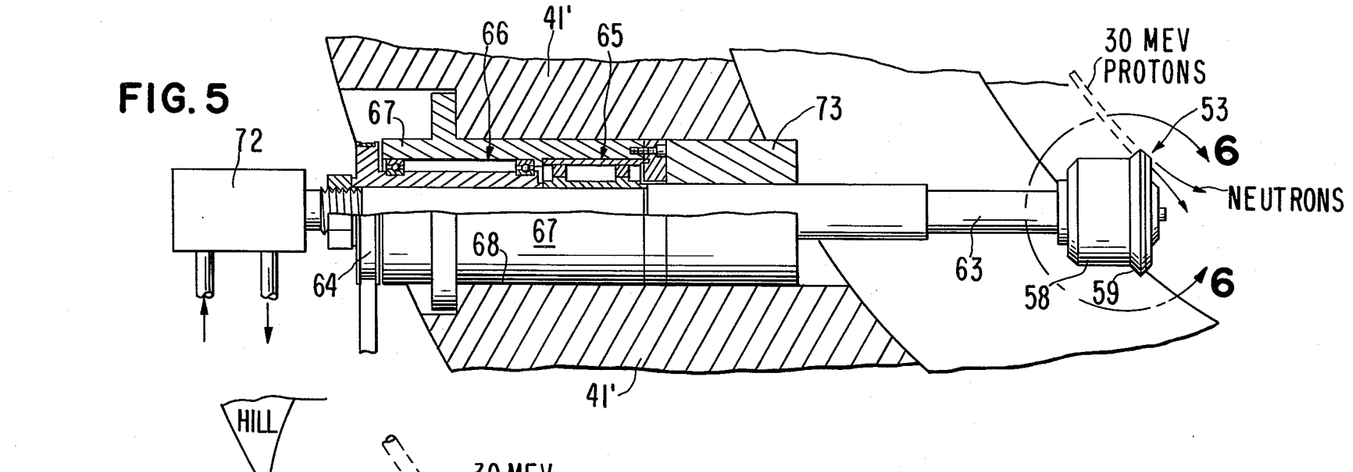
FIG. 5 is an enlarged sectional view of a portion of the structure of FIG. 3 taken along line 5—5 in the direction of the arrows.
Figure 6:
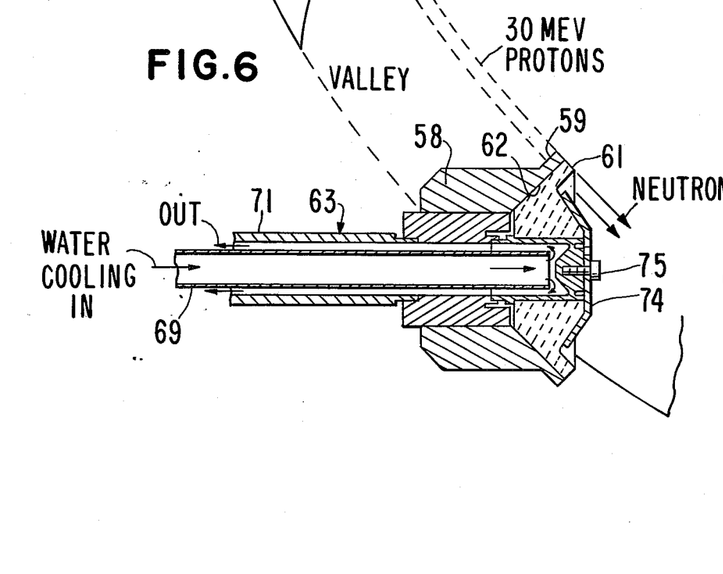
FIG. 6 is an enlarged longitudinal sectional view of a portion of the structure of FIG. 5 delineated by line 6—6.

Referring now to FIGS. 5-7 the target 53 is shown in greater detail. More particularly, the target 53 includes a cylindrical primary target member 58 made of a material having a relatively high neutron yield upon bombardment with protons of an energy above 15 MeV such as of beryllium, lithium or carbon-13, which serves to interact with the high energy protons, as they attenuate from 30 to 15 MeV, to produce high energy neutrons in a forward main lobe 21 having a center line which is generally tangent to the proton trajectories at their point of incidence with the target 58. The cylindrical target 58 includes an outwardly flared lip portion 59 having a surface perpendicular to the proton trajectories. A generally conical back-up member 61 is nested within a conical recess 62 in the target member 58. The back-up member 61 is made of a material that has a relatively low yield for neutrons such as carbon, graphite or gold, so as to absorb the remaining 15 MeV of energy of the proton beam without producing the copious flux of low energy neutrons which would otherwise be produced in beryllium, lithium or carbon-13. Thus, the skin dosage to the patient is reduced. 30 MeV protons produce about 19 MeV mean neutron energy from a 15 MeV thick beryllium target backed by a proton stopping material such as graphite and followed by 6 cm thick polyethylene filter to attenuate low energy neutrons.

In the same size cyclotron, the maximum deuteron energy from a beryllium target would be about 16 MeV and the mean neutron energy would be about 8 MeV. Thus, by using protons instead of deuterons in a compact water cooled cyclotron small enough for gantry mounting, a quite high energy neutron beam, adequate for radiotherapy treatment of the patient's torso, is obtained; with deuterons in the same compact cyclotron, the neutron energy is only penetrating enough for radiotherapy of the patient's head and neck and extremities.

The target is rotated by means of a shaft 63 to which a drive pulley 64 is affixed. The drive pulley is driven via a drive belt affixed to a second pulley driven from an electric motor. A ferrofluid rotary vacuum seal assembly 65 seals the rotatable target shaft 63 to the vacuum wall of the cylindrical yoke 41'. A bearing assembly 66 provides a rotatable bearing joint between the shaft 63 and the internal bore of a cylindrical housing 67 which is mounted in a cylindrical bore 68 in the yoke 41'. The shaft 63 includes coaxially mounted inner and outer hollow shaft portions 69 and 71 to provide an annular region between the two shafts through which a cooling fluid, such as water, flows. The fluid flows through the center of the inside hollow shaft 69 to the terminal end of the shaft 63 and returns in heat exchanging relation with the target members 58 and 61 so as to remove heat generated therein.

The coolant is fed into and withdrawn from the hollow shaft 63 via a rotary water joint and manifold 72 affixed to the outer end of the rotatable shaft 63. A cylindrical shielding member as of tungsten 73 is mounted within the inner end of the bore 68 for shielding the ferrofluid rotary vacuum seal 65 and other parts from radiation generated in the region of the target 58. The target members 58 and 61 are captured on the end of the shaft 63 via an end cap 74 held to the shaft 63 via cap screws 75.

Figure 8:
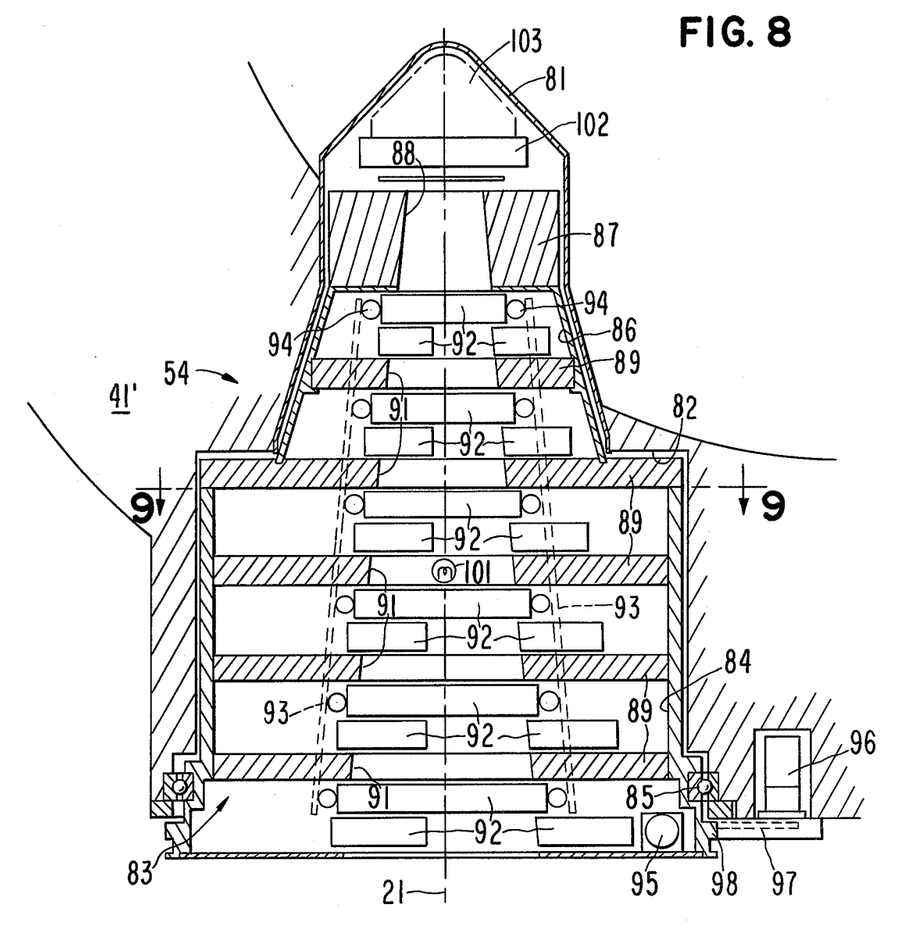
FIG. 8 is an enlarged sectional view of a portion of the structure of FIG. 3 delineated by line 8—8.
Figure 9:
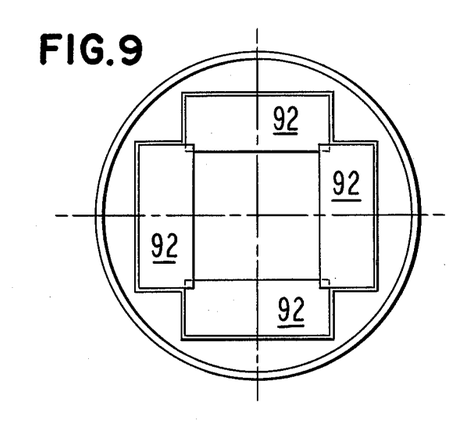
FIG. 9 is a sectional view of a portion of the structure of FIG. 8 taken along line 9—9 in the direction of the arrows.
Figure 10:
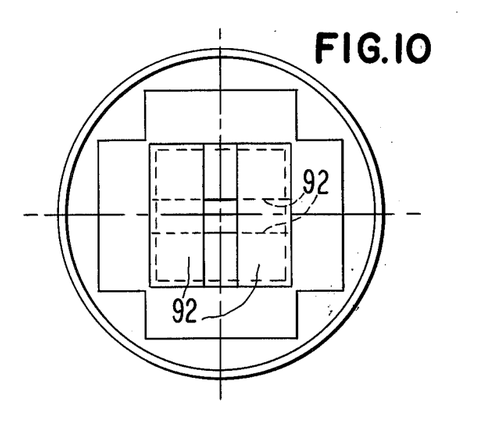
FIG. 10 is a view similar to that of FIG. 9 showing the components thereof in a different position.

Referring now to FIGS. 8-10 there is shown the neutron beam collimator 54. Collimator 54 includes a conical vacuum dome portion or neutron window 81 brazed into a cylindrical bore 82 in the cylindrical yoke portion 41' in axial alignment with the neutron beam path 21. A rotatable neutron beam collimator structure 83 is disposed within the bore 82 for collimating the neutron beam 21. The rotatable collimator structure 83 includes cylindrical side wall portion 84 rotationally mounted to the yoke 41' via the intermediary of a ball bearing assembly 85.

Cylindrical housing 84 includes an upper conical portion 86 closed off at its upper end by means of a primary neutron beam collimator 87, as of tungsten, having a conically shaped aperture 88 formed therein in axial alignment with the neutron beam 21. A plurality of centrally apertured auxiliary collimator plates 89, as of tungsten, are carried transversely within the rotatable housing 84. Each plate 89 has a rectangular central aperture 91 therein with dimensions corresponding to the maximum beam width of the neutron beam 21 to be collimated.

A plurality of jaw plates 92, such as four tungsten plates, are slidably translatably mounted to the plates 89 for movement radially of the longitudinal axis of the neutron beam 21 for changing the maximum cross sectional area of the neutron beam 21. The plates 92 are movable radially via the intermediary of a plurality of axially directed shafts 93 operable on drive shafts 94 coupled to the individual jaw plates 92 for affecting radial translation of the jaw plates 92 relative to the center line 21 of the neutron beam. A jaw drive motor 95 is carried within the housing 84 and operatively associated with the drive shafts 93 and 94 for affecting synchronized translation of the various jaw plates 92.

FIG. 9 shows the neutron beam aperture for a maximum cross section of the neutron beam 21 when the jaw plates are in their fully retracted position, whereas FIG. 10 shows a highly constricted position of the respective jaw plates 92 wherein the beam cross sectional area is a near minimum. The collimator 54 is therefore adjustable for adjusting the cross sectional area of the neutron beam 21 and is rotatable by means of a collimator rotation motor 96 carried from the yoke 41' coupled to the rotatable housing 94 via a gear train 97 driving a gear ring 98 carried from the lower end of the cylindrical housing 84.

A mirror 99 is mounted on the axis of the collimator 54 near the upper end thereof. A lamp 101 is disposed on the center line 21 of the neutron beam path and it projects its light up to the mirror 99 and thence the light is projected back through the collimator 54 to the patient treatment zone. The projected light as fed through the collimator 54, corresponds to the field of irradiation produced by the neutron beam 21. Thus, the neutron irradiation therapy machine 11 can be aligned with the proper region of the patient to be treated by the beam. A dual ionization chamber 102 is located in the collimator 54 for monitoring the intensity of the neutron beam 21. A neutron filter 103, such as of polyethylene, for filtering out low energy neutrons, is positioned between the ionization chamber 102 and the wall of the vacuum dome 81 for reducing skin dose in the patient. The neutron filter 103 preferably has increased thickness of attenuation coefficient near the beam axis and which decreases radially of the neutron beam axis for increasing the uniformity of the neutron intensity across, i.e., laterally, of the field of neutron irradiation in the patient treatment region.

A low energy neutron absorbing material, such as pressed wood particles or polyethylene, is placed into the spaces surrounding the movable jaws 92 for absorbing neutrons reflected into the regions between the inside wall of the housing 84 and the various movable plates 92. The rotatable collimator 54 permits the field of irradiation to be selected of a desired cross section and to be oriented to the patient treatment zone so as to irradiate only the desired regions.

What is claimed is:

1. In a neutron irradiation therapy machine for treating patients with a beam of neutrons:
   cyclotron means for accelerating protons to a high energy and for bombarding a target to generate a beam of high energy neutrons to be applied to the patient, said cyclotron means having magnet means for generating a magnetic field for interaction with the protons, said magnet means including a pair of pole portions spaced apart to define a magnetic gap therebetween and within which the magnetic field of said magnet means produces a force on said protons, said magnet means having a yoke means of ferromagnetic material interconnecting said pair of pole portions for providing a relatively low reluctance magnetic flux path for returning the magnetic flux to the respective pole portions, magnetomotive force generating mean coupled in magnetic flux exchanging relation with said pole portions for generating a magnetomotive force and for exciting said magnetic pole portions to opposite magnetic polarities,
   proton source means for supplying protons to the region between said pole portions to be accelerated to an energy in excess of 15 MeV, and
   gantry means for pivoting said cyclotron about a patient treatment region,
   neutron filter means disposed in the neutron beam between the target and the patient treatment region for attenuating relatively low energy neutrons of the beam.

2. The apparatus of claim 1 wherein said neutron filter means has an attenuation coefficient that falls off radially from the center of the beam whereby the uniformity of the neutron intensity is increased laterally of the field of neutron beam irradiation.

3. In a neutron irradiation therapy machine for treating patients with a beam of neutrons:
   cyclotron means for accelerating charged particles to a high energy and for bombarding a target to generate a beam of high energy neutrons to be applied to the patient, said cyclotron means having magnet means for generating a magnetic field for interaction with the charged particles, said magnet means including a pair of pole portions spaced apart to define a magnetic gap therebetween and within which the magnetic field of said magnet means produces a force on said charged particles, said magnet means having a yoke means of ferromagnetic material interconnecting said pair of pole portions for providing a relatively low reluctance magnetic flux path for returning the magnetic flux to the respective pole portions, non-superconducting magnetomotive force generating means coupled in magnetic flux exchanging relation with said pole portions for generating a magnetomotive force and for exciting said magnetic pole portions to opposite magnetic polarities, said magnetic yoke means generally enveloping said pole portions,
   gantry means for pivoting said cyclotron about an axis of revolution, said gantry means including a bearing structure having, a fixed stator portion and a rotor portion coupled to said cyclotron means for rotationally supporting said cyclotron means as said cyclotron means moves about said axis of revolution, support means for fixedly supporting said stator portion from a platform,
   patient table means supportively mounted from said rotor portion and extending generally parallel to said axis of revolution, and a second bearing structure rotationally supporting said patient table means from said rotor and permitting movement of said cyclotron about said patient table while retaining the position of said patient table fixed.

4. The apparatus of claim 3 including counterweight means mounted to said rotor portion in diametrically opposed relation to said cyclotron means for rotation with said rotor portion and for counterweighting the weight of said cyclotron means.

5. The apparatus of claim 3 including beam stopper means carried by said rotor portion in diametrically opposed relation to said cyclotron means and in the neutron beam for absorbing neutrons of the beam after passage thereof through the patient treatment zone.

6. The apparatus of claim 5 wherein said beam stopper means is made of pressed wood particles.

7. In a neutron irradiation therapy machine for treating patients with a beam of neutrons:
cyclotron means for accelerating charged particles to a high energy and for bombarding a target to generate a beam of high energy neutrons to be applied to the patient, said cyclotron means having magnet means for generating a magnetic field for interaction with the charged particles in said cyclotron means, said magnet means including a pair of pole portions spaced apart to define a magnetic gap therebetween and within which the magnetic field of said magnet means produces a force on said charged particles, said magnet means having a yoke means of ferromagnetic material interconnecting said pair of pole portions for providing a relatively low reluctance magnetic flux path for returning the magnetic flux to the respective pole portions, magnetomotive force generating means coupled in magnetic flux exchanging relation with said pole portions for generating a magnetomotive force and for exciting said magnetic pole portions to opposite magnetic polarities, said yoke means generally enveloping said pole portions, said cyclotron means including envelope means for defining an evacuable envelope within which said charged particles are accelerated, electrode means within said envelope to be excited with radio frequency power to produce a radio frequency electric field within said envelope for acting on said charged particles for acceleration thereof to high velocity, radio frequency transmission line means having an evacuable portion passing through said envelope means for transmitting radio frequency power from a source disposed external of said magnet means to said electrode means for excitation thereof, means for coupling a vacuum pump in gas communication with the interior of said envelope means via the intermediary of at least a portion of said evacuable radio frequency transmission line means for evacuation of said envelope means via at least a portion of said evacuable radio frequency transmission line means.

8. The apparatus of claim 7 wherein said transmission line means comprises a section of coaxial line having an outer electrical conductive tubular portion and a centrally disposed longitudinally directed inner electrically conductive portion.

9. In a neutron irradiation therapy machine for treating patients with a beam of neutrons:
accelerator means for accelerating charged particles to a high energy and for bombarding a target to generate a beam of high energy neutrons to be applied to the patient,
target means to be bombarded by said charged particles having an energy substantially greater than 15 MeV to produce a resultant stream of high energy neutrons, and wherein said target includes first and second constituent materials, said first constituent material comprising a relatively high neutron yield material when bombarded with protons of an energy greater than 15 MeV and said second target constituent material comprising a relatively low neutron yield material when bombarded with protons of an energy below 15 MeV.

10. The apparatus of claim 9 wherein said first constituent material of said target is selected from the group consisting of beryllium, lithium and carbon-13.

11. The apparatus of claim 9 wherein said second constituent material of said target is selected from the group consisting of carbon, graphite and gold.

12. The apparatus of claim 9 wherein said first constituent material of said target is selected from the group consisting of beryllium, lithium and carbon-13, and said second constituent material of said target is selected from the group consisting of carbon, graphite and gold.

13. The apparatus of claim 9 including means for rotating said target.

14. The apparatus of claim 13 including means for directing a fluid coolant through said rotatable target in heat exchanging relation therewith for cooling of said target in use.

15. In a neutron irradiation therapy machine for treating patients with a beam of neutrons:
accelerator means for accelerating charged particles to a high energy and for bombarding a target to generate a beam of high energy neutrons to be applied to the patient;
target means to be bombarded by the high energy charged particles to produce the resultant beam of high energy neutrons, shield means disposed adjacent said target means in neutron shielding relation thereto and having a charged particle passageway therein for passage of high energy charged particles through said shield means into said target means, and having a neutral particle exit passageway therein for passage of neutrons emanating from the target through said shield means in the direction of the neutron beam.

16. The apparatus of claim 15 wherein said shield means is made of tungsten.

17. The apparatus of claim 16 wherein said charged particle beam entrance passageway and said neutron beam exit passageway comprises a slot in said shield means, said accelerator means including a magnet means for generating a magnetic field in a gap between a pair of magnetic pole portions enclosed by an evacuable ferromagnetic yoke, said slot lying in a plane coplanar with a plane between said pair of pole portions, and including a second neutron shield means disposed inside of said yoke adjacent a main lobe of neutron flux emanating from said target and in a plane coplanar with said slot in said first shield means for shielding neutrons passing through said first slot means and straying out of the desired neutron beam.

18. The apparatus of claim 17 wherein said second shield means is made of tungsten.

19. In a neutron irradiation therapy machine for treating patients with a beam of neutrons:
cyclotron means for accelerating charged particles to a high energy and for bombarding a target to generate a beam of high energy neutrons to be applied to the patient, said cyclotron means having magnet means for generating a magnetic field for interaction with the charged particles, said magnet means including a pair of pole portions spaced apart to define a magnetic gap therebetween and within which the magnetic field of said magnet means produces a force on said charged particles, said magnet means including a yoke means of ferromagnetic material interconnecting said pair of pole portions for providing a relatively low reluctance magnetic flux path for returning the magnetic flux to the respective pole portions, magnetomotive force generating means coupled in magnetic flux exchanging relation with said pole portions for generating a magnetomotive force and for exciting said magnetic pole portions to opposite magnetic polarities, said yoke means generally enveloping said pole portions, collimator means disposed in the neutron beam path downbeam from said target for collimating the beam of neutrons to be applied to the patient treatment zone; said collimator means including a neutron absorbing means having a neutron beam passageway therein, and means for varying the size of said neutron beam passageway for varying the cross sectional area of the neutron beam as applied to the patient treatment zone.

20. The apparatus of claim 19 wherein said means for varying the size of said neutron beam passageway includes a set of neutron absorbing jaw means spaced about the periphery of the neutron beam for defining the cross sectional size of said neutron beam passageway, and means for moving said jaw means radially relative to the central axis of said neutron beam path for varying the size of said neutron beam passageway.

21. The apparatus of claim 20 wherein said neutron absorbing jaw means are made of tungsten.

22. The apparatus of claim 20 including a plurality of said sets of neutron absorbing jaw means arranged serially along the neutron beam path.

23. The apparatus of claim 20 including means for absorbing low energy neutrons in said collimator.

24. The apparatus of claim 23 wherein said means for absorbing low energy neutrons is made of a material selected from the group of pressed wood particles and polyethylene.

25. The apparatus of claim 19 wherein said yoke means includes a neutron beam bore therein in alignment with said neutron beam, and wherein said collimator means is mounted within said neutron beam bore and said yoke means.

26. The apparatus of claim 20 including, means for rotating said collimator means about an axis of revolution intersecting the central axis of said neutron beam.

* * * * *